United States Patent
Heo et al.

(10) Patent No.: US 12,152,011 B2
(45) Date of Patent: Nov. 26, 2024

(54) USNIC ACID DERIVATIVE HAVING TSLP SECRETION INHIBITORY ABILITY AND USE THEREOF

(71) Applicant: SEOUL NATIONAL UNIVERSITY HOSPITAL, Seoul (KR)

(72) Inventors: Chan Yeong Heo, Yongin-si (KR); So Min Kang, Seongnam-si (KR); Da Som Jeon, Seongnam-si (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 819 days.

(21) Appl. No.: 17/284,306

(22) PCT Filed: Oct. 10, 2019

(86) PCT No.: PCT/KR2019/013305
§ 371 (c)(1),
(2) Date: Apr. 9, 2021

(87) PCT Pub. No.: WO2020/076100
PCT Pub. Date: Apr. 16, 2020

(65) Prior Publication Data
US 2021/0395214 A1     Dec. 23, 2021

(30) Foreign Application Priority Data

Oct. 10, 2018  (KR) ................. 10-2018-0120342
Oct. 8, 2019   (KR) ................. 10-2019-0124901

(51) Int. Cl.
*A61P 37/08*   (2006.01)
*A23L 33/10*   (2016.01)
*A61P 17/02*   (2006.01)
*C07D 307/91*  (2006.01)

(52) U.S. Cl.
CPC ............ *C07D 307/91* (2013.01); *A23L 33/10* (2016.08); *A61P 17/02* (2018.01); *A61P 37/08* (2018.01); *A23V 2002/00* (2013.01)

(58) Field of Classification Search
CPC ......... C07D 307/91; A61P 37/08; A61P 17/02
See application file for complete search history.

(56) References Cited

FOREIGN PATENT DOCUMENTS

| CN | 102526019 A | * | 7/2012 |
| WO | WO 2012/131347 A1 | | 10/2012 |
| WO | WO 2017/134594 A1 | | 8/2017 |

OTHER PUBLICATIONS

Erba et al., New esters of R −(+)-usnic acid, ( IL Farmaco 53), 1998, pp. 718-720 (Year: 1998).*
Sun et al., Erba et al., New esters of R â(+)-usnic acid, ( IL Farmaco 53), 1998, pp. 718-720 (Year: 1998).*
CN102526019A English Translation, Espacenet (Year: 2012).*
Indra A.K., Expert review of Proteomics 2013, vol. 10, Issue 4, pp. 309-311.
Shtro, A. A. et al., Bioorganic & Medicinal Chemistry, 2014, vol. 22 pp. 6826-6836.
Kang, S et al. Journal of Investigative Dermatology, May 2019, vol. 139, Issue 5, S13.

* cited by examiner

*Primary Examiner* — Sarah Pihonak
*Assistant Examiner* — Mikhail O'Donnel Robinson
(74) *Attorney, Agent, or Firm* — Stein IP, LLC (57) ABSTRACT

The present invention relates to a novel Usnic acid derivative exhibiting an inhibitory effect on TSLP secretion or pharmaceutically acceptable salts thereof, and a use thereof.

8 Claims, 11 Drawing Sheets

A. Control

Before​ ​ ​ ​ After

Before​ ​ ​ ​ After

Before

After

Before

After

[FIG. 7e]

E. Tranilast 100 ug/ml

Before

After

[FIG. 8a]

A. Control x 200 x 400

E. Tranilast 100 ug/ml x 200            x 400

USNIC ACID DERIVATIVE HAVING TSLP SECRETION INHIBITORY ABILITY AND USE THEREOF

CROSS-REFERENCE WITH RELATED APPLICATION(S)

This application is a national stage of International Application No. PCT/KR2019/013305 filed on Oct. 10, 2019, which claims the benefit of priority based on Korean Patent Application No. 10-2018-0120342 filed on Oct. 10, 2018 and Korean Patent Application No. 10-2019-0124901 filed Oct. 8, 2019. All contents published in the documents are included as part of this specification.

TECHNICAL FIELD

The invention relates to a usnic acid derivative having the ability to inhibit TSLP secretion, and more particularly, to a usnic acid derivative and its use.

BACKGROUND TECHNOLOGY

Atopic dermatitis, also referred to as an advanced country-type incurable disease, is a globally common disease that can occur at any age, and 70% to 95% of infants under 5 years of age. In Korea, the problem of atopic dermatitis has already reached a serious social and medical level. According to various reports, about 15% of all Koreans are atopic dermatitis patients, of which 18 to 22 per 100 infants aged 0 to 4 are atopic patients. In addition, more than 50% of patients with atopic dermatitis develop an 'atopic march' that develops allergic rhinitis and asthma.

The exact pathophysiology of allergic diseases including atopic dermatitis as described above is not yet fully understood, but it is thought that immunological and environmental factors may be involved along with the genetic predisposition. Since the symptoms of immune imbalance appear in common in patients with allergic diseases such as Asthma, allergic rhinitis, atopic dermatitis, many studies are being conducted from an immunological point of view.

On the other hand, the underlying cause of allergic diseases is known as immune imbalance, which is the result of various biological signals. The highest protein of this abnormal signaling is the thymic stromal lymphopoietin (TSLP) cytokine. When the allergen penetrates into the body, substances such as TSLP stimulate dendritic cells to react, and in this process, symptoms of allergic diseases such as atopic dermatitis and asthma appear.

These TSLPs, as IL-7-like cytokines, were first discovered in the culture medium of thymic stromal cells. (skin, respiratory, digestive, eye, etc.), and is mainly secreted from skin epidermal cells and skin epithelial cells. According to recent studies, in addition to epithelial cells and epidermal keratinocytes, TSLP is also secreted from mast cells, airway smooth muscle, fibroblasts, and dendritic cells to control the immune response. It is known that overexpression causes immune imbalance.

According to published literature, it was found that TSLP protein and mRNA were increased in lesions of atopic dermatitis patients, and showed severe allergic disease in human and animal models (mouse) that increased TSLP expression in the skin (Steven F. Ziegler). et al., J Allergy Clin Immunol, 2012; 130: 845-52). In addition, TSLP was detected in bronchial lavage fluid of asthmatic patients, and it was reported that there was a correlation between the sensitivity of the disease and the increase of TSLP expression in airway epidermal cells. And, It has been found that due to TSLP secreted from skin cells, allergic inflammatory reactions are intensified and the onset of asthma is accelerated upon exposure to antigens (Juan et al., Journal of Investigative Dermatology, 2012).

Causes that promote TSLP secretion include viruses, bacteria and bacterial products, protease allergens, inflammatory cytokines, chemicals, and physical irritation (scratching), and if over-expressed, it causes an immune imbalance. The mechanism causing the immune imbalance is as described below.

TSLP receptor (TSLPR) is mainly expressed in hematopoietic cells, and most often expressed in dendritic cells (DC). The survival period of dendritic cells increases due to TSLP, which increases the expression of class II major histocompatibility complex II and co-stimulatory molecules CD86 and CD40, and Th2 CD4+T cells and naive (naive). The secretion of CCL17 and CCL22, which increases CD4+T cell influx, respectively, is also increased. Furthermore, OX40L expression, which increases Th2 differentiation, increases, and IL-12 expression, which is involved in Th1 differentiation, decreases, and TSLP consequently promotes the mechanism by which dendritic cells induce Th2 response. In addition, TSLP deepens immune imbalance by promoting the influx of eosinophils, mast cells, and natural killer T cells and secretion of cytokines such as IL-13.

DETAILED DESCRIPTION OF THE INVENTION

Technical Task

In order to develop an effective therapeutic agent for atopic dermatitis, the present inventors studied the previously well-known usnic acid, and as a result, it was confirmed that the usnic acid derivative of the present invention inhibits the expression of TSLP and various cytokines, by which present invention has been completed.

The object of the invention is to provide a compound represented by Formula 1 or a pharmaceutically acceptable salt thereof.

Another object of the invention is to provide a pharmaceutical composition for the prevention or treatment of allergic diseases or skin scars having TSLP secretion inhibitory ability containing a compound represented by Formula 1 or a pharmaceutically acceptable salt thereof as an active ingredient.

Another object of the invention is to provide a cosmetic composition for alleviating or improving allergic diseases or skin scars having TSLP secretion inhibitory ability containing a compound represented by Formula 1 or a pharmaceutically acceptable salt thereof as an active ingredient.

Another object of the invention is to provide a health functional food composition for alleviating or improving allergic diseases or skin scars having TSLP secretion inhibitory ability containing a compound represented by Formula 1 or a pharmaceutically acceptable salt thereof as an active ingredient.

Another object of the invention is to provide a method for preventing, treating, alleviating or improving allergic diseases or skin scars, comprising administering to an individual a compound represented by Formula 1 or a pharmaceutically acceptable salt thereof.

Another object of the invention is to provide a use of the compound represented by Formula 1 or a pharmaceutically acceptable salt thereof for the prevention, treatment, alleviation or improvement of allergic diseases or skin scars.

Another object of the present invention is to provide a use of a pharmaceutical composition containing a compound represented by Formula 1 or a pharmaceutically acceptable salt thereof for use in the prevention or treatment of allergic diseases or skin scars.

Another object of the invention is to provide a use of a cosmetic composition containing a compound represented by Formula 1 or a pharmaceutically acceptable salt thereof for use in allergic disease or skin scar relief or improvement.

Another object of the invention is to provide a use of a health functional food composition containing a compound represented by Chemical Formula 1 or a pharmaceutically acceptable salt thereof for allergic disease or skin scar relief or improvement.

Technical Solution

In order to solve the above problems, a usnic acid derivative represented by the following formula (1) or a pharmaceutically acceptable salt thereof is provided.

<Formula 1>

In addition, in order to solve the above problem, a pharmaceutical for the prevention or treatment of allergic diseases or skin scars containing the usnic acid derivative represented by Formula 1 or a pharmaceutically acceptable salt thereof as an active ingredient and having TSLP secretion inhibitory ability The composition is provided.

The "thymic stromal lymphopoietin (TSLP)" of the invention is an IL-7-like hematopoietic cytokine, which is produced in epithelial cells, stromal cells, and mast cells, and is an important factor controlling the body's immune response. Therefore, when TSLP is over-expressed (hypersecreted) in the human body, including skin cells, it may cause an immune imbalance, thereby causing the onset and intensification of allergic diseases.

"Allergic disease" of the present invention means an allergic predisposition, that is, a disease caused by an allergic reaction (immune hypersensitivity reaction). Although the exact cause of the disease has not yet been identified, immune imbalances are observed in most patients with allergic diseases, and thus therapeutic agents or treatment methods through immune imbalance control are being actively studied.

In the invention, these allergic diseases include atopic dermatitis, asthma, allergic rhinitis, allergic conjunctivitis, allergic dermatitis, and urticaria (hives). And it may be one or more selected from the group consisting of food allergy, but is not limited thereto.

Atopic dermatitis of the invention is a chronic recurrent inflammatory skin disease that begins mainly in infancy or childhood, and is a disease accompanied by pruritus (itch), dry skin, and characteristic eczema.

The skin scar of the invention is arising from the biological process of wound healing in the skin tissue, and non-limiting examples of the skin scar include abrasions, scars caused by abrasions, and alike.

Usnic acid derivative represented by Chemical Formula 1 (MW 604.61) of the present is a compound synthesized by reacting usnic acid and cinnamoyl chloride with each other. More specifically, it is characterized in that it is produced through the reaction process of Scheme 1 as follows.

<Reaction Scheme 1>

The composition containing the usnic acid derivative represented by Formula 1 or a pharmaceutically acceptable salt thereof as an active ingredient may have the ability to prevent or treat allergic diseases or skin scars caused by immune imbalance.

"Prevention" of the invention means any action of inhibiting or delaying a disease by administration of a composition containing the compound represented by Formula 1 or a pharmaceutically acceptable salt thereof. In addition, the term "treatment" used in the invention refers to all actions in which symptoms of a disease are improved or cured by administration of a composition containing a compound represented by Formula 1 or a pharmaceutically acceptable salt thereof.

The compound represented by Formula 1 of the present invention can be used in the form of a pharmaceutically acceptable salt, and such salts including acid addition salts formed by pharmaceutically acceptable free acids or metal salts formed by bases.

Inorganic acid and organic acid may be used as the free acid, and hydrochloric acid, sulfuric acid, bromic acid, sulfurous acid or phosphoric acid may be used as the inorganic acid. Examples of the metal salt include an alkali metal salt or an alkaline earth metal salt, and sodium, potassium, or calcium salts are useful.

For administration, the composition of the invention may contain a pharmaceutically acceptable carrier, excipient, or diluent in addition to the above-described active ingredients. Examples of the carrier, excipient and diluent include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, Polyvinylpyrrolidone, water, methylhydroxybenzoate, propylhydroxybenzoate, talc, magnesium stearate, and mineral oils.

The "pharmaceutical composition" of the invention is formulated in the form of oral dosage forms such as powders, granules, tablets, capsules, suspensions, emulsions, syrups, aerosols, etc., external preparations, suppositories or sterile injectable solutions according to a conventional method can be used. Specifically, when formulated, it may be prepared using a diluent or excipient such as a filler, a weight agent, a binder, a wetting agent, a disintegrant, a surfactant, etc. that are commonly used. Solid preparations for oral administration include, but are not limited to, tablets, pills, powders, granules, capsules, and alikes. Such a solid preparation may be prepared by mixing at least one excipient, for example, starch, calcium carbonate, sucrose, lactose, gelatin, and the likes with the compound represented by Formula 1 or a pharmaceutically acceptable salt thereof. Furthermore, in addition to simple excipients, lubricants such as magnesium stearate and talc may also be used. It can be prepared by adding various excipients, such as wetting agents, sweetening agents, fragrances, preservatives, and the like, in addition to oral liquids and liquid paraffins. Formulations for parenteral administration include sterilized aqueous solutions, non-aqueous solvents, suspensions, emulsions, lyophilized formulations, and tasks. As the non-aqueous solvent and suspending agent, propylene glycol, polyethylene glycol, vegetable oils such as olive oil, injectable esters such as ethyl oleate, and the like may be used. As a base for suppositories, witepsol, macrosol, Tween 61, cacao butter, laurin, glycerogelatin, and the like may be used.

A suitable dosage of the composition of the invention varies depending on the condition and weight of the patient, the degree of the disease, the form of the drug, and the time, but can be appropriately selected by a person skilled in the production. The daily dosage of the acceptable salt is preferably 1 mg/kg to 500 mg/kg, and may be administered once to several times a day, if necessary.

In order to achieve the above other object, the present invention contains as an active ingredient a usnic acid derivative represented by the following formula (1) or a pharmaceutically acceptable salt thereof, and has the ability to inhibit TSLP secretion, for allergic disease or skin scar relief It provides a cosmetic composition.

<Formula 1>

The cosmetic composition containing the compound represented by Formula 1 of the invention or a pharmaceutically acceptable salt thereof as an active ingredient may inhibit over-expression of TSLP in the skin, and the allergic diseases include atopic dermatitis, asthma, It may be one or more selected from the group consisting of allergic rhinitis, allergic conjunctivitis, allergic dermatitis, urticaria, and food allergy.

In addition to the active ingredients, the cosmetic composition of the invention may include commonly accepted ingredients, and may include conventional adjuvants such as antioxidants, stabilizers, solubilizers, vitamins, pigments and fragrances, and a carrier.

The cosmetic composition of the invention may be prepared in any formulation conventionally prepared in the art, for example, solution, suspension, emulsion, paste, gel, cream, lotion, powder, soap, surfactant-containing cleansing, Oil, powder foundation, emulsion foundation, wax foundation, and may be formulated as a spray, but is not limited thereto. In more detail, it may be prepared in the form of a flexible lotion (skin), nutritional lotion (milk lotion), nutritional cream, massage cream, essence, eye cream, cleansing cream, cleansing foam, cleansing water, pack, spray, or powder.

When the formulation of the invention can be a paste, cream or gel, animal oil, vegetable oil, wax, paraffin, starch, tragacanth, cellulose derivative, polyethylene glycol, silicone, bentonite, silica, talc, or zinc oxide may be used as a carrier component.

When the formulation of the invention is a powder or spray, lactose, talc, silica, aluminum hydroxide, calcium silicate, or polyamide powder may be used as a carrier component. In particular, in the case of a spray, additional chlorofluorohydrocarbon, propane/May contain propellants such as butane or dimethyl ether.

When the formulation of the invention is a solution or emulsion, a solvent, a solubilizing agent or an emulsifying agent is used as a carrier component, such as water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or fatty acid ester of sorbitan.

When the formulation of the invention is a suspension, as a carrier component, a liquid diluent such as water, ethanol or propylene glycol, an ethoxylated isostearyl alcohol, a suspending agent such as polyoxyethylene sorbitol ester and polyoxyethylene sorbitan ester, microcrystals Sex cellulose, aluminum metahydroxide, bentonite, agar or tragacanth, and the likes can be used.

When the formulation of the present invention is a surfactant containing cleansing, as a carrier component, aliphatic alcohol sulfate, aliphatic alcohol ether sulfate, sulfosuccinic acid monoester, isethionate, imidazolinium derivative, methyltaurate, sarcositate, fatty acid amide Ether sulfates, alkylamidobetaines, fatty alcohols, fatty acid glycerides, fatty acid diethanolamides, vegetable oils, lanolin derivatives, or ethoxylated glycerol fatty acid esters may be used.

The present invention contains a compound represented by the following Formula 1 or a pharmaceutically acceptable salt thereof as an active ingredient in order to achieve the another object, and for allergic disease or skin scar relief or improvement having TSLP secretion inhibitory ability It provides a health functional food composition.

<Formula 1>

The above health functional food composition includes various nutrients, vitamins, minerals (electrolytes), flavoring agents such as synthetic flavoring agents and natural flavoring agents, coloring agents and heavy weight agents (cheese, chocolate, etc.), pectic acid and salts thereof, alginic acid and salts thereof. Organic acids, protective colloidal thickeners, pH adjusters, stabilizers, preservatives, glycerin, alcohols, carbonates used in carbonated beverages, and the like. In addition, it may contain flesh for the manufacture of natural fruit juices, synthetic fruit juices and vegetable beverages. These components may be used independently or in combination. In addition, the health functional food composition can be any one of meat, sausage, bread, chocolate, candy, snack, confectionery, pizza, ramen, gum, ice cream, soup, beverage, tea, functional water, drink, alcohol and vitamin complex In addition, the health functional food composition may additionally contain food additives, and whether it is suitable as a "food additive" is determined according to the general rules of the Food Additive Code approved by the Ministry of Food and Drug Safety and general test methods, etc., unless otherwise specified. It is judged according to the standards and standards for the item.

Items listed in the "Food Additives Code", for example, chemical synthetic products such as ketones, glycine, potassium citrate, nicotinic acid, and cinnamic acid, natural additives such as reduced pigment, licorice extract, crystalline cellulose, high cooling pigment, guar gum, etc., L-Mixed preparations, such as a sodium glutamate preparation, a noodle-added alkali agent, a preservative preparation, and a tar color preparation, etc. are mentioned.

At this time, the content of the compound represented by Formula 1 or a pharmaceutically acceptable salt thereof according to the present invention added to the food in the process of preparing the health functional food composition can be appropriately added or subtracted as needed, preferably food It is preferable to add so that 1 to 15 parts by weight is included in 100 parts by weight.

The invention provides a use comprising the step of administering a compound represented by Formula 1 or a pharmaceutically acceptable salt thereof to an individual in order to achieve the above other object, prevention, treatment, alleviation or improvement of allergic diseases or skin scars.

The invention provides a use of the compound represented by Chemical Formula 1 or a pharmaceutically acceptable salt thereof for the prevention, treatment, alleviation or improvement of allergic diseases or skin scars in order to achieve the above other object.

In order to achieve the above other object, the invention provides a use of a pharmaceutical composition containing a usnic acid derivative represented by Formula 1 or a pharmaceutically acceptable salt thereof for the prevention or treatment of allergic diseases or skin scars.

In order to achieve the above other objects, the invention provides a use of a cosmetic composition containing a usnic acid derivative represented by Formula 1 or a pharmaceutically acceptable salt thereof for allergic disease or skin scar relief or improvement. to provide.

The invention provides the use of a health functional food containing a usnic acid derivative represented by Formula 1 or a pharmaceutically acceptable salt thereof to alleviate or improve allergic diseases or skin scars in order to achieve the above other object.

Effects of the Invention

According to the invention, since the usnic acid derivative or a pharmaceutically acceptable salt thereof has an excellent effect of inhibiting the secretion of TSLP, which is an immune response factor, the composition according to the present invention is atopic dermatitis, asthma, allergic rhinitis, allergic conjunctivitis. It can be used for the prevention, treatment, alleviation and improvement of allergic diseases or skin scars, including allergic dermatitis.

FORMS FOR THE IMPLEMENTATION OF THE INVENTION

In order to help understand the invention, it will be described in detail with reference to examples. However, the following examples are provided to more completely describe the present invention to those with average knowledge in the art, and only exemplify the contents of the present invention, so that the scope of the present invention is limited to the following examples. It is not.

Example 1. Synthesis and Separation of Usnic Acid Derivatives (Hereinafter UA-CA)

Dissolve 0.85 g (2.47 mmole) of R-(+)-Usnic acid in 50 ml of DCM, cool with an ice bath, and slowly add 1.0 ml (7.4 mmol, 3.0 eq) of TEA and 0.9 g (5.4 mmol, 2.2 eq) of Cinnamoyl chloride. After adding, the mixture was stirred at 0° C. for 20 minutes. Thus, it was synthesized through the following reaction formula.

<Reaction Scheme 2>

After confirming the completion of the reaction by TLC, the reaction solution was diluted in 60 ml of water and extracted with DCM. The organic layer was dried over anhydrous sodium sulfate, filtered, and the solvent was evaporated off under reduced pressure. The remaining residue was purified by silica gel column chromatography (developing solvent: n-Hex/EtOAc=5/1) to obtain 1.19 g (79%) of the target compound (A) in an orange solid state.

Figure 1A:
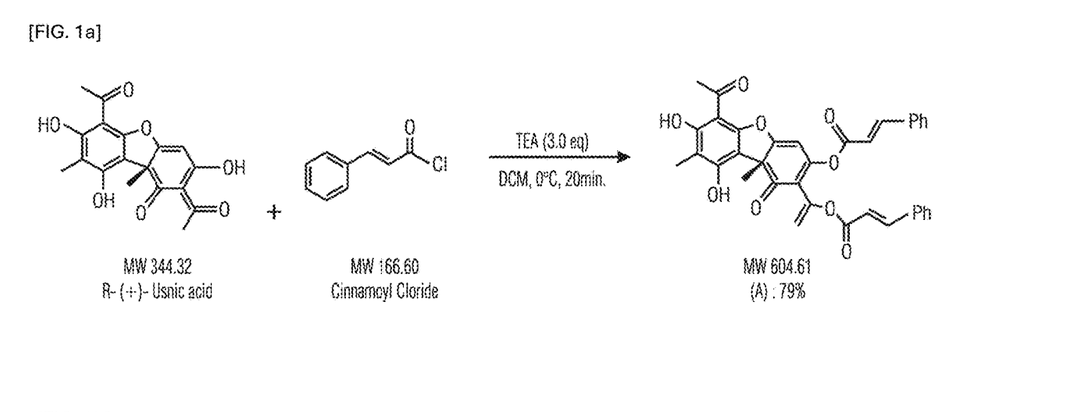
FIG. 1A is a reaction scheme for preparing a usnic acid derivative of the present invention.
Figure 1B:
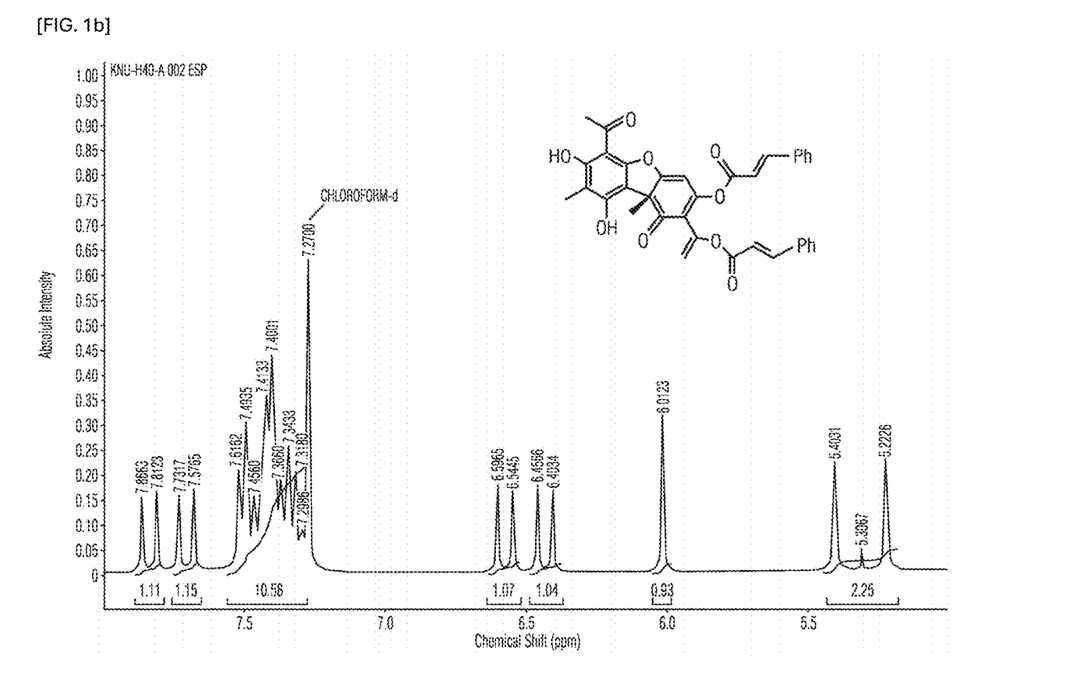
FIG. 1B is a result of NMR analysis of the usnic acid derivative of the present invention.
Figure 2:
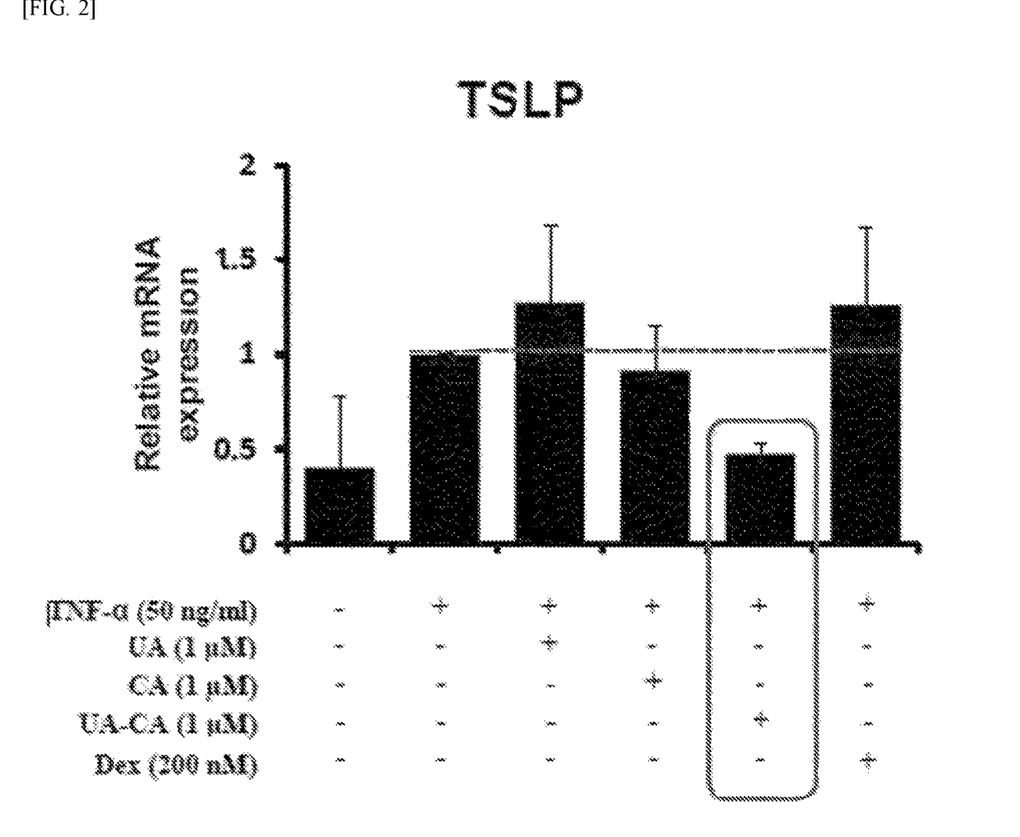
FIG. 2 is a real-time PCR result for measuring the change in the expression level of the TSLP gene.
Figure 3:
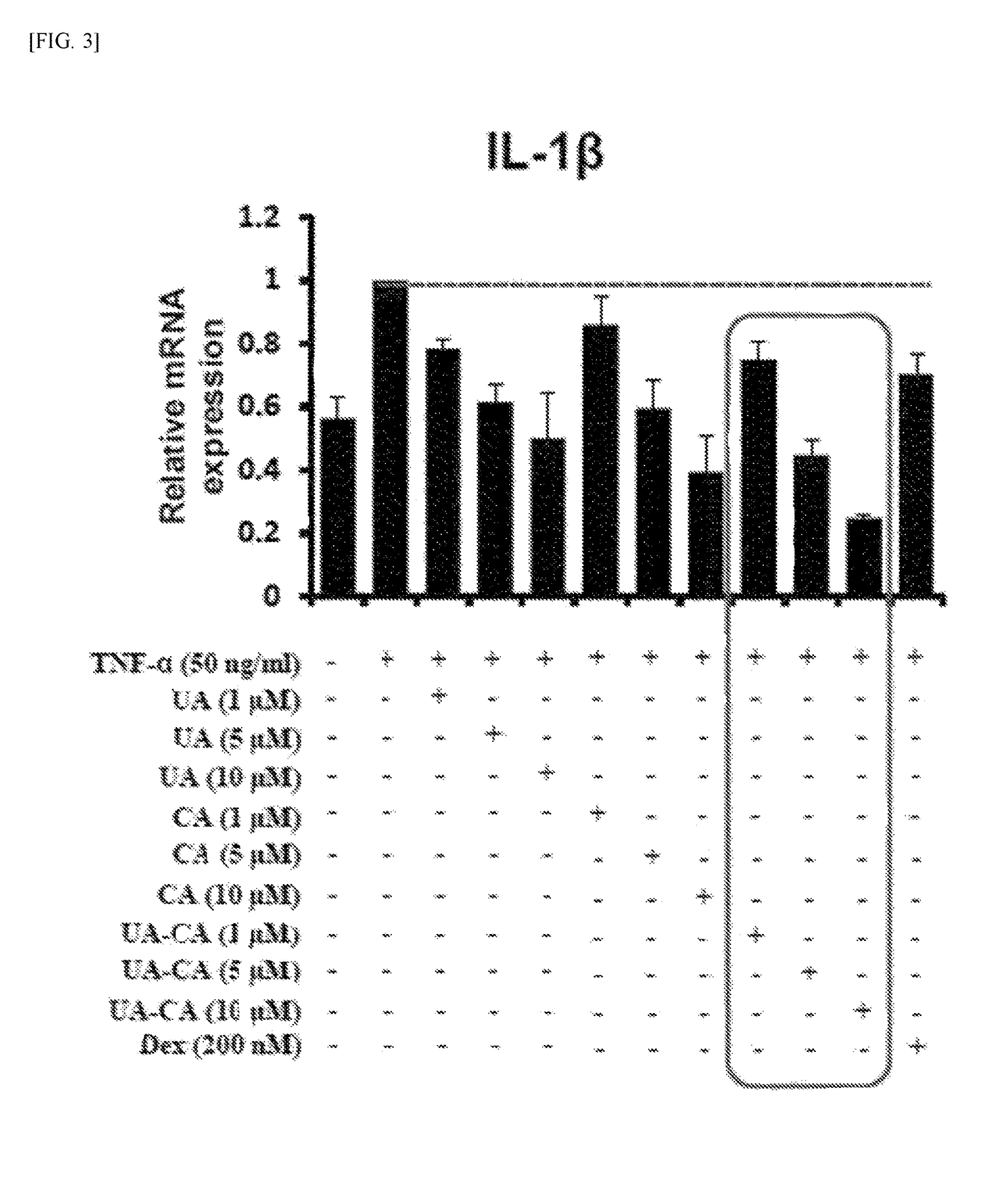
FIG. 3 is a real-time PCR result for measuring the change in the expression level of the IL-1β gene.
Figure 4:
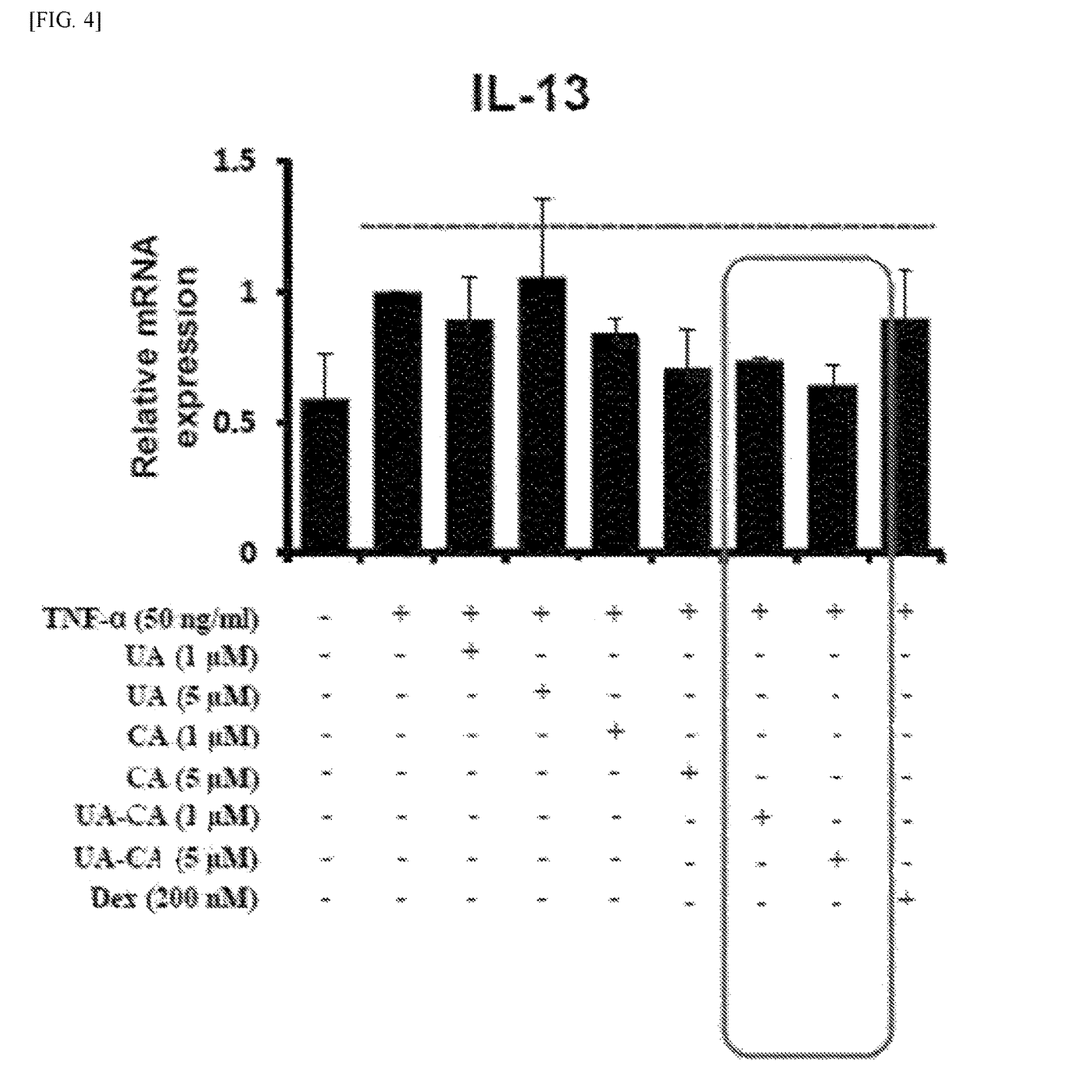
FIG. 4 is a real-time PCR result for measuring the change in the expression level of the IL-13 gene.
Figure 5:
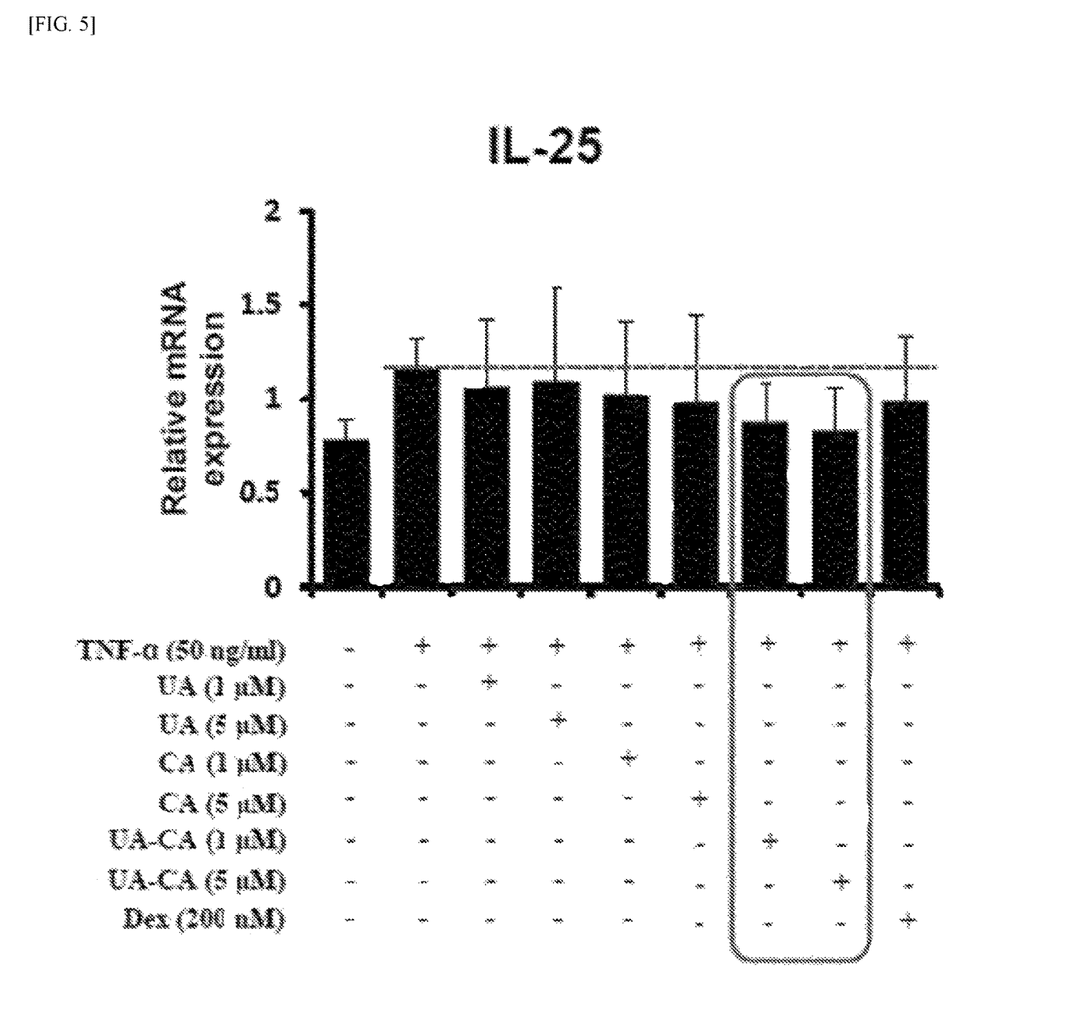
FIG. 5 is a real-time PCR result for measuring the change in the expression level of the IL-25 gene.
Figure 6:
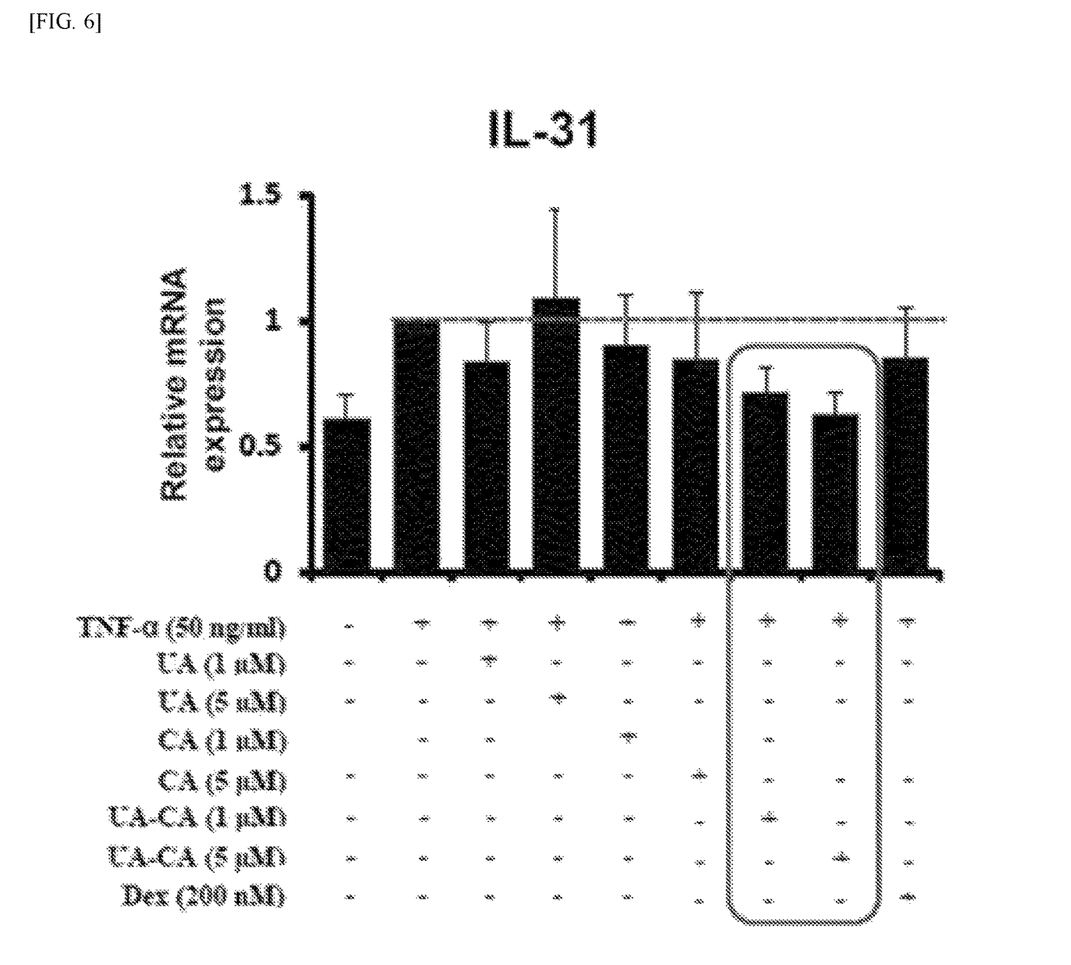
FIG. 6 is a real-time PCR result for measuring the change in the expression level of the IL-31 gene.
Figure 7A:
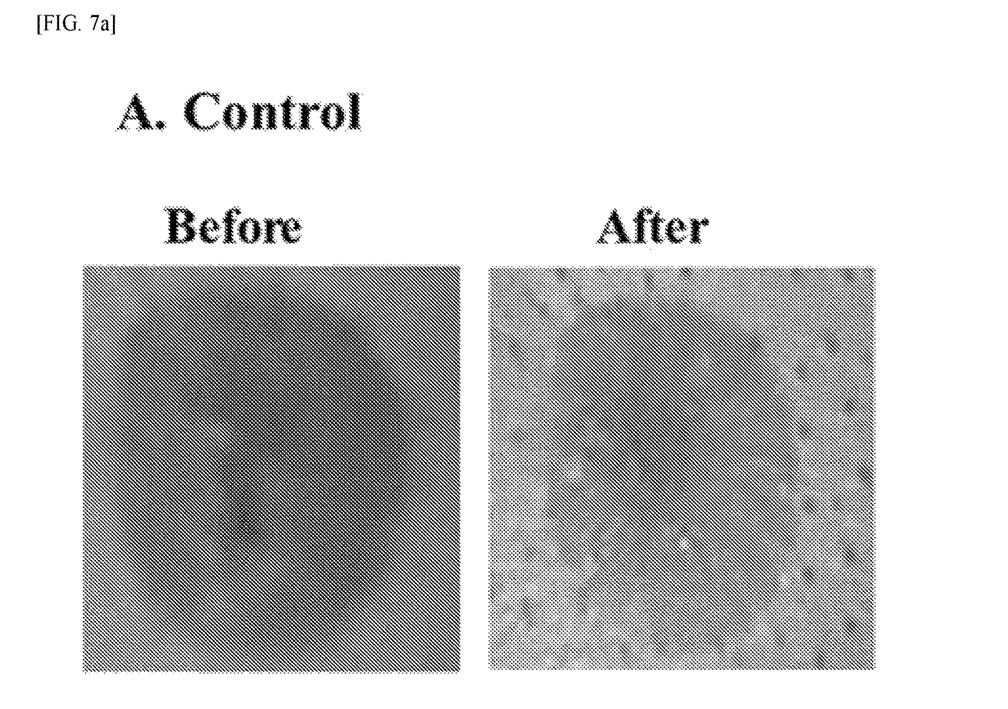
FIG. 7A to 7E are results of biopsy and histological examination to confirm the effect of alleviating hypertrophic scars.
Figure 7B:
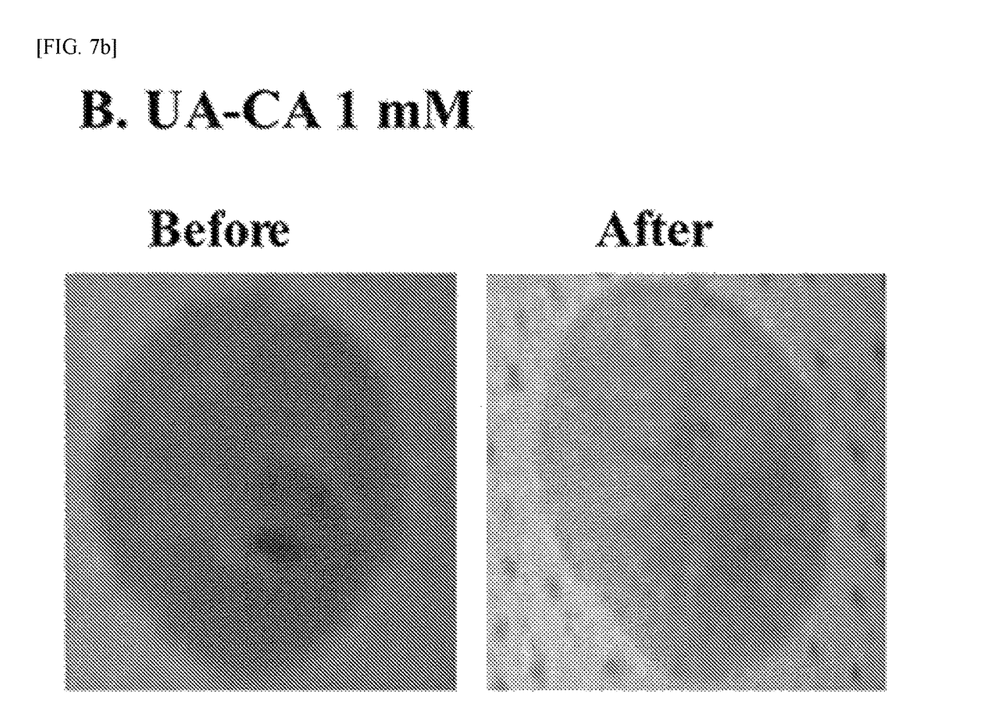
Figure 7C:
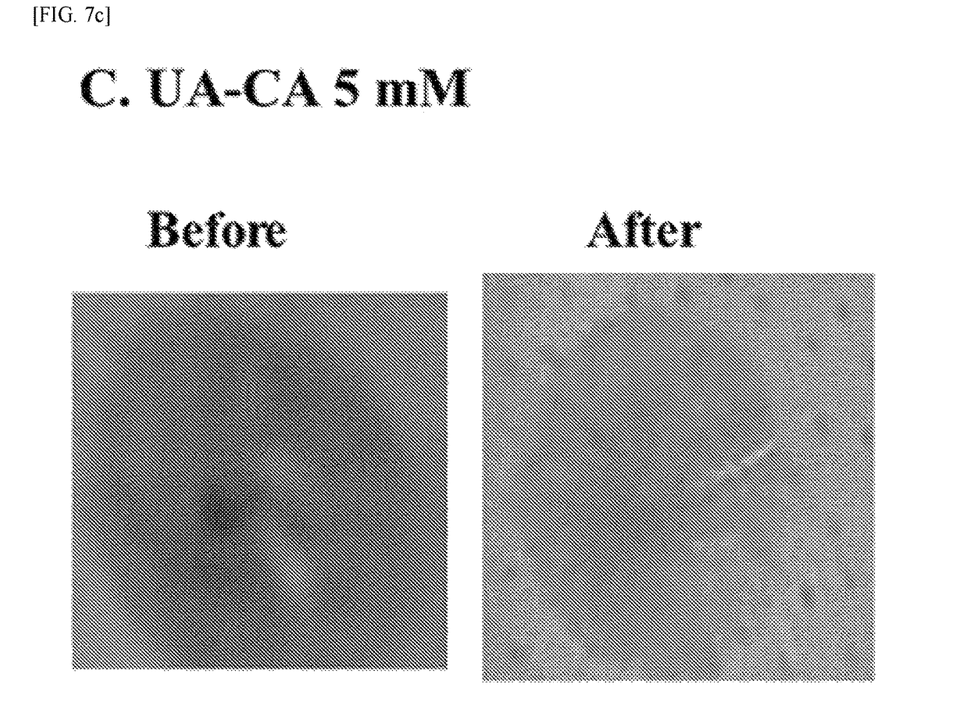
Figure 7D:
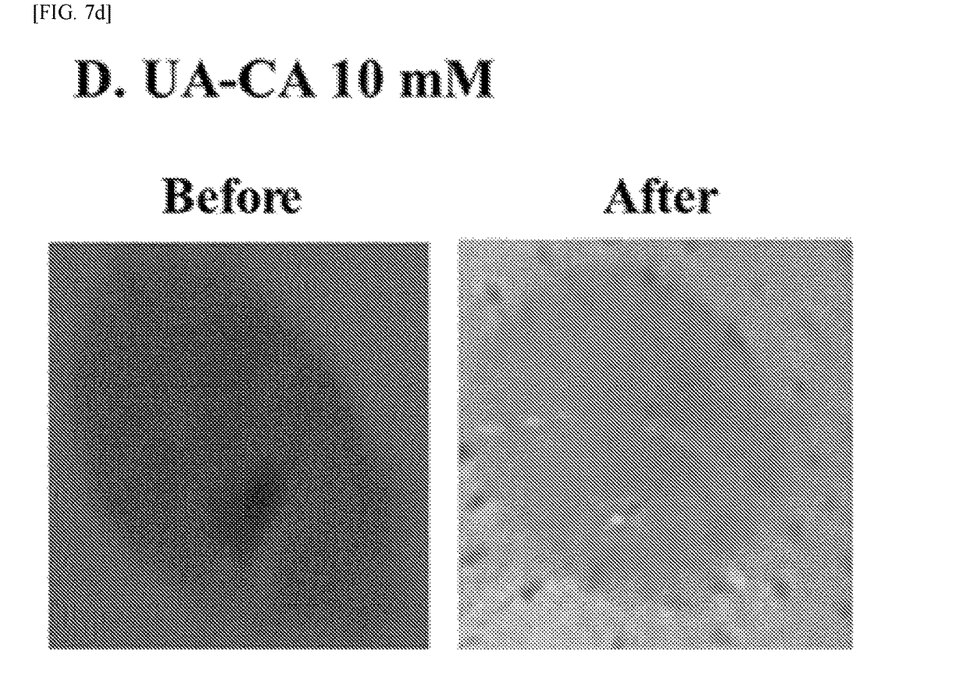
Figure 7E:
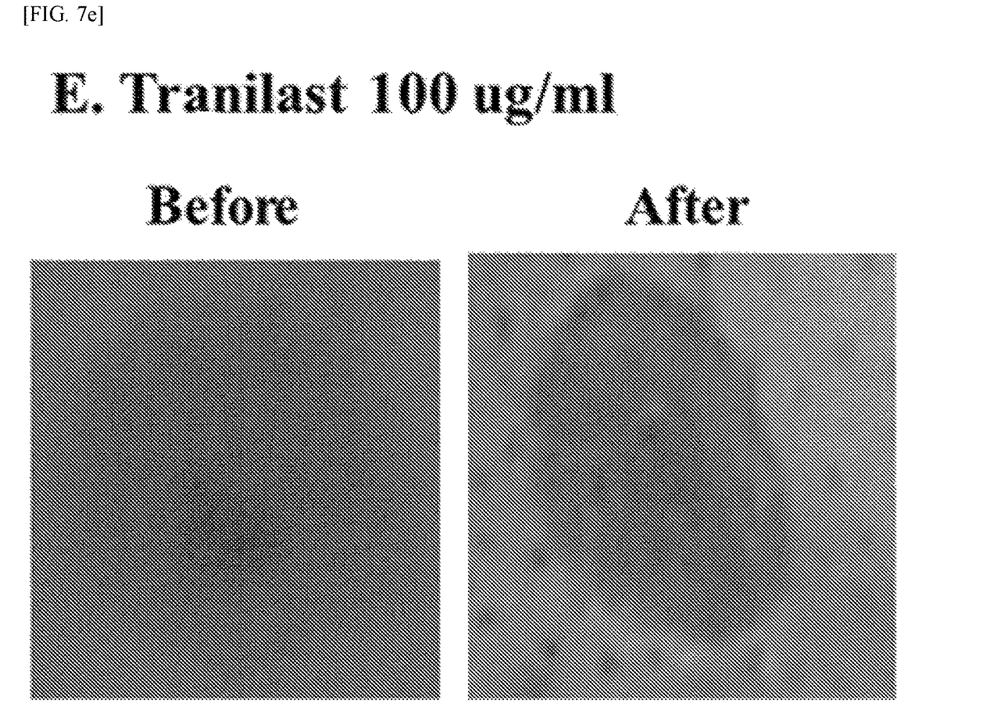
Figure 8A:
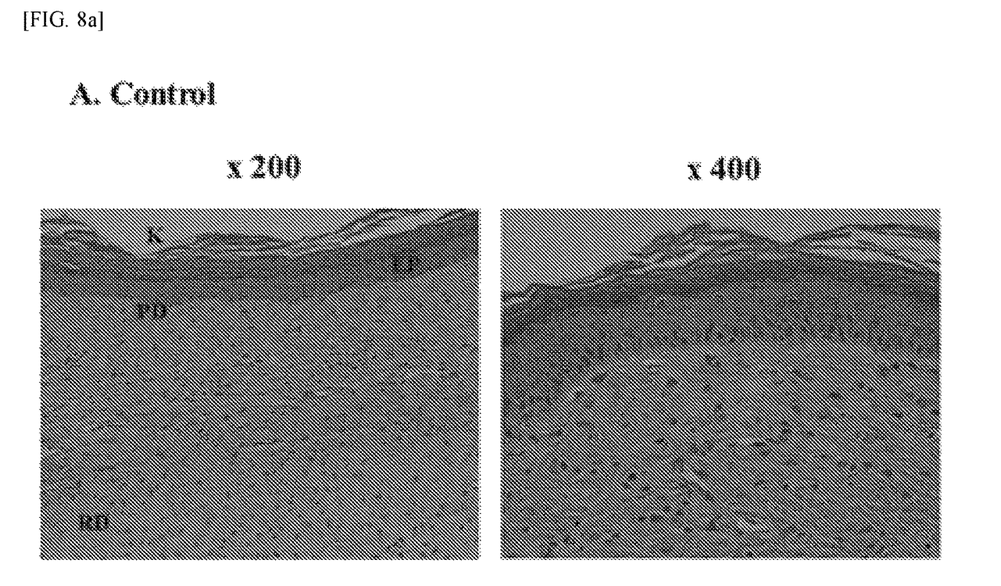
FIG. 8A to 8E are pathological examination results of skin tissue to confirm the effect of relieving hypertrophic scars (K: keratin layer, EP: epidermis, PD: papillary dermis, RD: reticular dermis).
Figure 8B:
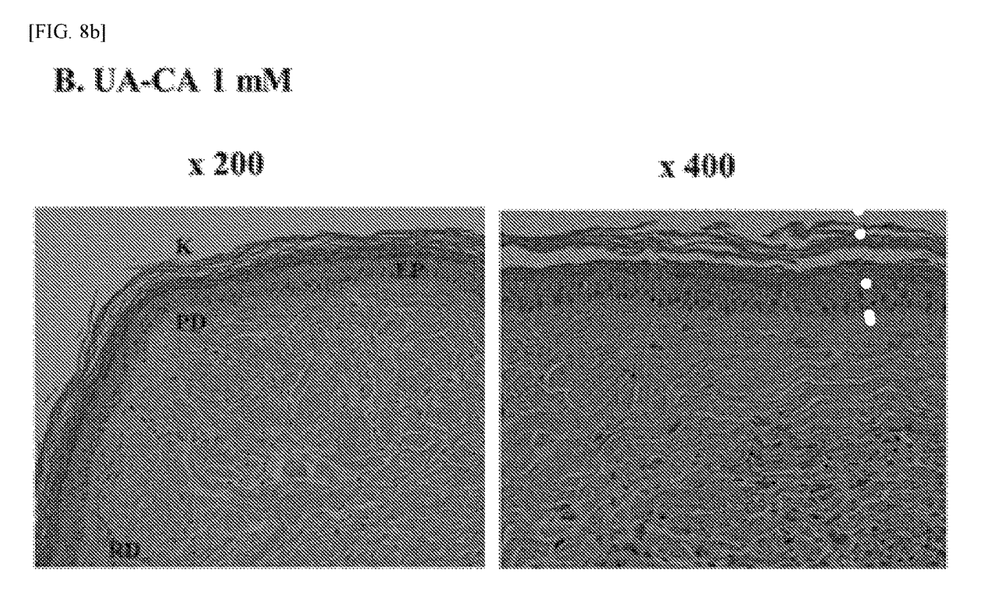
Figure 8C:
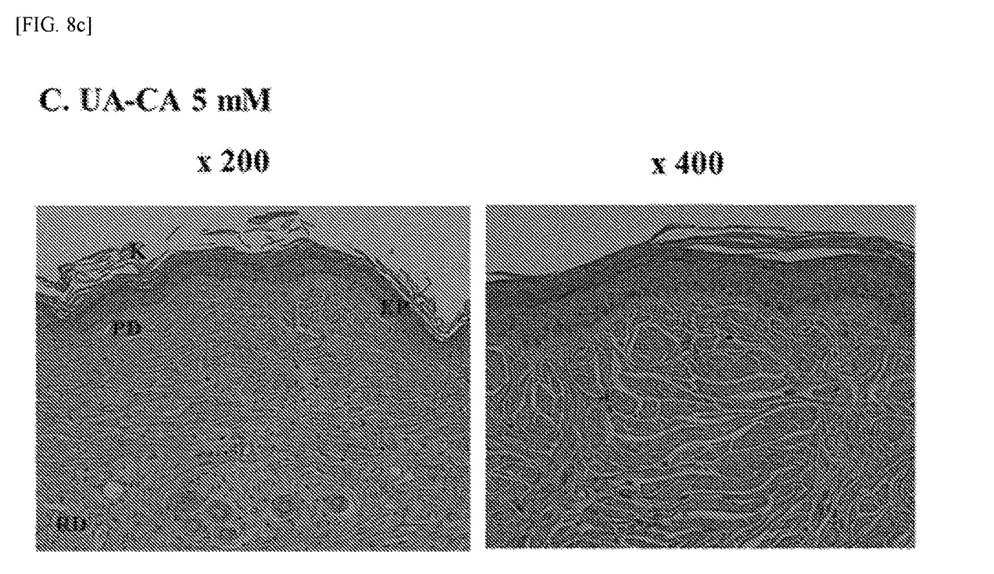
Figure 8D:
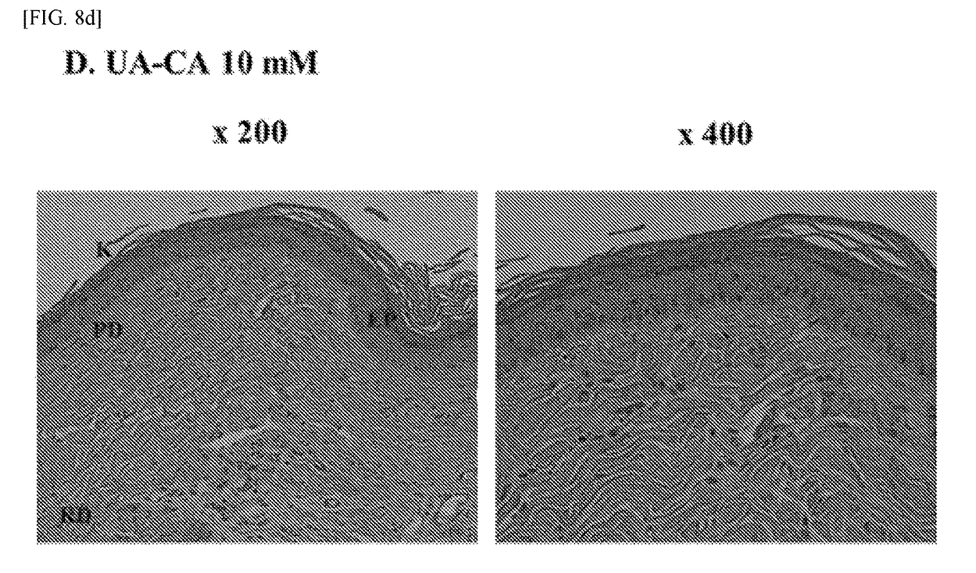
Figure 8E:
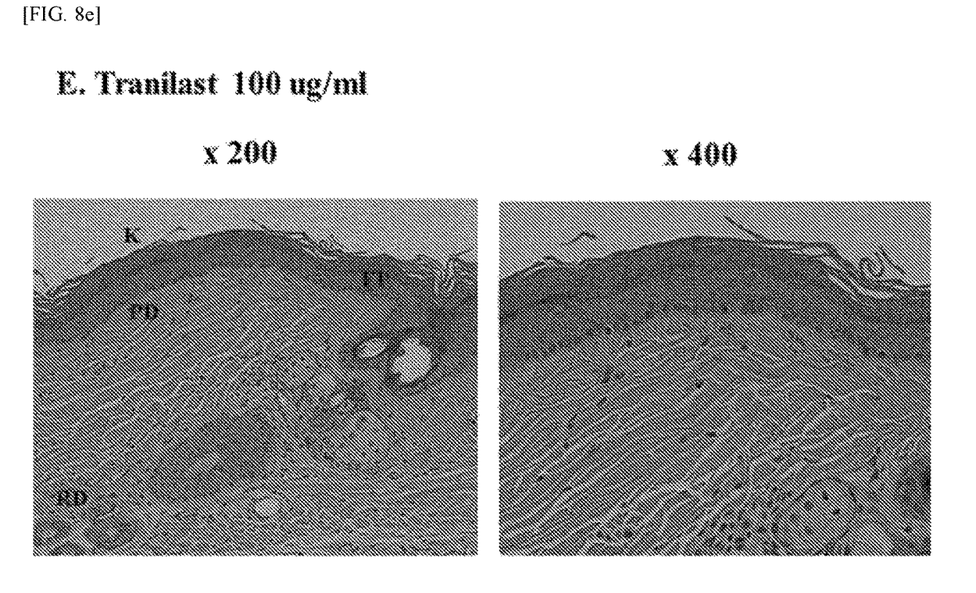

The NMR analysis results for Compound A are as follows (see FIG. 1b).

(A): 1H NMR (500 MHz, CDCl3): δ 13.33 (s, 1H, OH), 10.54 (s, 1H, OH), 7.84 (d, 1H), 7.70 (d, 1H), 7.29-7.51 (m, 10H), 6.58 (d, 1H), 6.42 (d, 1H), 6.01 (s, 1H), 5.60 (d, J=54.2 Hz, 2H), 2.67 (s, 3H), 2.12 (s, 3H), 1.87 (s, 3H)

Example 2. Cytokine Gene Expression Level Experiment of Usnic Acid Derivatives

<1> Culture of Human Keratinocyte Line

HaCaT, an immortalized human keratinocyte line, was prepared in DMEM (Dulbecco's modified Eagle's media) medium containing glutamine 2 mM, penicillin 400 U/ml, streptomycin 50 mg/ml, and 10% FBS at 37° C. with 5% CO2. Incubated in the atmosphere. For the treatment of UA-CA, the cells were cultured with 80% confluence and then cultured for 24 hours without addition of FBS. After cultivation, the cells were washed with phosphate buffered saline (PBS), and the prepared UA-CA was added to the medium.

<2> Confirmation of the Expression Level of Atopy-Related Inflammatory Cytokine Gene Through qRT-PCR To confirm the mRNA expression of atopic dermatitis-related inflammatory cytokines (TSLP, IL-1β, IL-13, IL-25, IL-31), inflammatory cytokines were induced through TNF-a stimulation in HaCaT cells, and then UA Expression control by -CA treatment was confirmed. Total RNA was isolated using RNAiso Plus (Takara Bio Inc., Shiga, Japan), and 2 μg of total RNA was converted to cDNA using RevertAid First Strand cDNA Synthesis Kit (Thermo Scientific, MA, USA). 36B4 cDNA, an indicator of quantification of cytokines and endogenous standards, was performed using a 7500 real-time polymerase chain reaction (PCR) system (Applied Biosystems, Foster City, CA, USA). This test method can detect RT-PCR products directly without downstream processing, and it was possible to perform monitoring the increase in fluorescence of dye-labeled DNA probes specific for each factor, along with a probe specific for the 36B4 gene used as an endogenous control. TB Green Premix Ex Taq (Takara Bio Inc., Shiga, Japan) was used in all samples, and the reaction was performed in a final reaction volume of 10 μl. Sequences of forward and reverse primers for cytokines and 36B4 were designed as shown in [Table 1] below. qRT-PCR cycling conditions were 50° C. for 2 minutes, 95° C. for 10 minutes, 95° C. for 15 seconds, and 64° C. for 40 seconds. Data were analyzed using the 2-DDCT (delta delta C [T]) method. After normalization to 36B4, the relative mRNA levels were determined. Each experiment was repeated at least three times, and data are presented as mean SEM.

TABLE 1

| | |
|---|---|
| h36B4-forward primer | 5'-TCG ACA ATG GCA GCA TCT AC-3' |
| h36B4-reverse primer | 5'-TGA TGC AAC AGT TGG GTA GC-3' |
| hTSLP-forward primer | 5'-TAT GAG TGG GAC CAA AAG TAC CG-3' |
| hTSLP-reverse primer | 5'-GGG ATT GAA GGT TAG GCT CTG G-3' |
| hIL-1β-forward primer | 5'-CTC CAG GGA CAG GAT ATG GA-3' |
| hIL-1β-reverse primer | 5'-TCT TTC AAC ACG CAG GAC AC-3' |
| hIL-13-forward primer | 5'-CCT CAT GGC GCT TTT GTT GAC-3' |
| hIL-13-reverse primer | 5'-TCT GGT TCT GGG TGA TGT TGA-3' |
| hIL-25-forward primer | 5'-CTC CTG TCT CTT CCT CTT TTC C-3' |
| hIL-25-reverse primer | 5'-TGC ACC CAA AGT AGA TGC TC-3' |
| hIL-31-forward primer | 5'-CAC GTT GCC CGT CCG TTT A-3' |
| hIL-31-reverse primer | 5'-TCT TCG AGA GGG ACT GTA ATT CC-3' |

As a result of the experiment, it was found that the expression level of the cytokine gene was significantly increased in the TNF-a treatment group compared to the TNF-a treatment group. And, it was found that the expression level of cytokine genes was dependently decreased. Therefore, it can be seen that the UA-CA of the present invention has an action of reducing the expression of cytokines related to atopic dermatitis (by treatment with TNF-a) (see FIGS. 2 to 6).

Example 3. Experiment of Confirming the Scar Alleviation Efficacy of the Usnic Acid Derivative Against Hypertrophic Scars In order to confirm the efficacy of Usnic acid derivatives in relieving hypertrophic scars, the degree of scar relief by UA-CA treatment in hypertrophic scar samples was confirmed through histological comparison and pathological examination of skin tissue after biopsy.

A total of 4 rabbits weighing 3.5 kg (N2W conventional, female, 30 weeks old) were reared for a week in an environment of 21±1° C. 12-hour light/dark cycle, and the experiment was carried out. After anesthesia by intravenous administration of ketamine (60 mg/kg)+xylazine (5 mg/kg), both ears of the rabbit were sufficiently sterilized with betadine, and 5 wounds each with a diameter of 6 mm were made with a biopsy punch and a neck collar was applied. Management and supervision were made to become a hypertrophic scar model for 2 weeks after wound surgery. After confirming the hypertrophic scar model, the test material was treated twice a week for 2 weeks (untreated hypertrophic scar sample (Control), hypertrophic scar sample treated with 1, 5, and 10 mM UA-CA, 100 Thickening scar samples treated with ug/ml tranilast). After 2 weeks, visual evaluation and biopsy of the wound area were performed, followed by H&E staining, and then the changes in epidermal thickness were compared at 200 times and 400 times under a microscope.

As a result, as shown in FIGS. 7A to 7E, it was confirmed that scar relief was more advanced in the UA-CA-treated sample compared to the untreated hypertrophic scar, and in particular, the hypertrophic scar treated with the positive control tranilast Compared with, the samples treated with 1 mM UA-CA had similar scar relief, and the samples treated with 10 mM UA-CA had better scar relief efficacy.

In addition, as shown in FIGS. 8A to 8E, it was confirmed that the thickness of the epidermis became thinner as the scar alleviation proceeded more in the UA-CA-treated sample compared to the untreated thickening scar.

The invention claimed is:

1. Usnic acid derivative represented by the following formula (1)

<Formula 1> or a pharmaceutically acceptable salt thereof.

2. A pharmaceutical composition for the prevention or treatment of allergic diseases or skin scars containing the usnic acid derivative of claim 1 or a pharmaceutically acceptable salt thereof as an active ingredient.

3. The pharmaceutical composition of claim 2, wherein the allergic disease is atopic dermatitis, asthma, allergic rhinitis, allergic conjunctivitis, allergic dermatitis, urticaria, hives or food allergy.

4. A cosmetic composition for alleviating or improving allergic diseases or skin scars containing the usnic acid derivative of claim 1 or a pharmaceutically acceptable salt thereof as an active ingredient.

5. The cosmetic composition of claim 4, wherein the allergic disease is atopic dermatitis, asthma, allergic rhinitis, allergic conjunctivitis, allergic dermatitis, urticaria, hives or food allergy.

6. A health functional food composition for alleviating or improving allergic diseases or skin scars containing the usnic acid derivative of claim 1 or a pharmaceutically acceptable salt thereof as an active ingredient.

7. The health functional food composition of claim 6, wherein the allergic disease is atopic dermatitis, asthma, allergic rhinitis, allergic conjunctivitis, allergic dermatitis, urticaria, hives or food allergy.

8. A method for preventing, treating, alleviating or improving allergic diseases or skin scars, comprising the step of administering to an individual the usnic acid derivative of claim 1 or a pharmaceutically acceptable salt thereof.

* * * * *